United States Patent
Gallicchio

(10) Patent No.: US 6,663,389 B1
(45) Date of Patent: Dec. 16, 2003

(54) IMPLANT FOR ARTIFICIAL TEETH

(76) Inventor: Antonio Gallicchio, Via Giuseppe Lacchin, 32, 33077 Scaile (IT)

( * ) Notice: Subject to any disclaimer, the term of this patent is extended or adjusted under 35 U.S.C. 154(b) by 0 days.

(21) Appl. No.: 09/936,234

(22) PCT Filed: Jan. 27, 2000

(86) PCT No.: PCT/EP00/00630
§ 371 (c)(1),
(2), (4) Date: Sep. 12, 2001

(87) PCT Pub. No.: WO00/54696
PCT Pub. Date: Sep. 21, 2000

(30) Foreign Application Priority Data

Mar. 16, 1999 (IT) .................................... UD99A0056

(51) Int. Cl.⁷ ................................................ A61C 8/00
(52) U.S. Cl. ...................................... 433/173; 433/174
(58) Field of Search ................................. 433/172, 173, 433/174, 175, 176

(56) References Cited

U.S. PATENT DOCUMENTS

| | | |
|---|---|---|
| 3,466,748 A | 9/1969 | Christensen |
| 4,957,437 A | 9/1990 | Shimura et al. ............. 433/169 |
| 5,049,073 A * | 9/1991 | Lauks ......................... 433/169 |
| 5,092,771 A | 3/1992 | Tatum, III .................. 433/173 |
| 5,199,873 A * | 4/1993 | Schulte et al. .............. 433/173 |
| 5,213,500 A * | 5/1993 | Salazar et al. .............. 433/169 |
| 5,695,335 A * | 12/1997 | Haas et al. .................. 433/169 |
| 5,782,918 A * | 7/1998 | Klardie et al. .............. 433/172 |
| 5,823,776 A * | 10/1998 | Duerr et al. ................ 433/173 |

\* cited by examiner

Primary Examiner—Cary E. O'Connor
(74) Attorney, Agent, or Firm—Guido Modiano; Albert Josif; Daniel O'Byrne

(57) ABSTRACT

An implant for artificial teeth, including: an intrabony insert or implant (1) which is designed to be inserted in a fixed manner in the jawbone and is provided with a cavity (10); an artificial tooth assembly with a tooth stump (3) for the respective artificial tooth and a stem to be inserted and fixed in the cavity of the intrabony insert or implant; the cavity (10) of the intrabony implant has an undercut annular recess (12) below and above which there are hole portions (11,13, 14) having a smaller diameter, one (11) of the hole portions, above the recess (12), being interrupted by at least one longitudinal access slot (121) for the passage of at least one lug of the stem of the tooth stump (3) by axial sliding and subsequent rotation, the outer upper end of the intrabony implant being polygonal, the tooth stump (3) protruding beyond the lug with a polygonal region for the insertion of a polygonal annular bush for the mutual locking of the stump (3) with respect to the intrabony implant (1) so as to prevent rotation.

7 Claims, 4 Drawing Sheets

IMPLANT FOR ARTIFICIAL TEETH

BACKGROUND OF THE INVENTION

The present invention relates to an implant for artificial teeth.

The invention is used particularly but not exclusively in the field of prosthodontics, where artificial teeth are fitted in the human jaw by inserting a metallic implant for each tooth in the jawbone and by fixing a corresponding artificial tooth therein.

Prostheses for artificial teeth are already known which use:

- at least one artificial tooth support, which is designed to replace the root of the removed tooth and can be stably inserted in the jawbone at the region where the artificial tooth is to be applied, said support being generally made of titanium and being hollow (this support is commonly known as intrabony implant);
- at least one structure for supporting an interchangeable artificial tooth with a tang for engagement in the recess of the tooth support (commonly known as stump).

The stump and the intrabony implant are coupled by fixing means which, in the current art, are mainly constituted by axial screw means whose drawback is that they are complicated and expensive as well as difficult to apply.

Furthermore, the screw coupling easily loosens due to the stresses produced by chewing and this can even lead to breakage of the threads, with possibly severe damage.

A solution to this problem, proposed by the same Applicant, is disclosed in Italian patent application UD 97 A 00084, which provides for an implantation system for artificial teeth of the type which provides for a hollow intrabony insert or implant to be inserted in a fixed manner in the jawbone and an artificial tooth assembly which has a stump associated with means for fixing in said insert.

According to this solution, in the cavity of the intrabony implant there are at least two annular ridges which are spaced and whose annular shape is interrupted so that the interruption is formed in one ridge in opposition to the interruption of the other ridge.

The stump also has a protrusion which enters and engages the cavity and has two lugs at the interruptions in order to pass beyond the ridges by axial insertion coupling and, by rotation, into corresponding underlying annular slots, engaging below them so as to prevent extraction.

In this manner, the problems are partially solved; in particular, greater safety against the danger of losing the artificial tooth is achieved.

Even this solution, however, is complicated and particularly expensive due to the provision of the double annular undercut acting as safety coupling with rotary insertion coupling, which is necessary in any case to avoid the danger of disengagement.

Such complexity is further increased by the limited size of the implants, also in view of the fact that the presence of the double undercut reduces the resisting cross-section, with the danger of failure.

Therefore, although the above solution is theoretically valid, it still entails a structure which is complicated and therefore, despite the higher safety that it provides, is expensive and therefore applicable only to users who can afford this higher cost.

Another drawback that occurs in conventional solutions is due to the fact that the annular thickness of the intrabony implant (outside diameter with respect to the cavity diameter) is necessarily reduced, since the outside diameter is limited by the thickness of the jawbone in the implantation area, and therefore there is the risk of excessively weakening the tang of the stump or the wall of the intrabony implant that accommodates the tang.

In any case, in view of the extremely intense stresses applied by the jaw during chewing, there is the danger that the former or the latter may break.

DISCLOSURE OF THE INVENTION

The aim of the present invention is, therefore, to eliminate the drawbacks noted above in conventional types, providing a new implant for artificial teeth in which the fixing means are even quicker and simpler than current ones yet are reliable and have low-production costs.

In accordance with the invention, there is provided an implant assembly, comprising: an intrabony implant which is designed to be inserted in a fixed manner in the jawbone and is provided with a cavity; an artificial tooth assembly with a tooth stump for the respective artificial tooth, said tooth stump having a lower stem to be inserted and fixed in said cavity of said intrabony implant, and a said tooth stump having an upper protrusion for engagement with an artificial tooth; which is characterized in that said cavity of said intrabony implant has an undercut annular recess below and above which there are hole portions having a smaller diameter, one of said hole portions, above said recess, being interrupted by at least one longitudinal access slot for the passage of at least one lug of the stem of said tooth stump by axial sliding and subsequent rotation of said stem in said recess, the outer upper end of said intrabony implant being polygonal, said tooth stump protruding above said lug with said protrusion having a polygonal region for the insertion of a polygonal annular bush for the mutual locking of said stump with respect to said intrabony implant so as to prevent rotation.

BRIEF DESCRIPTION OF THE DRAWINGS

Further characteristics and advantages of the invention will become apparent from the detailed description of some embodiments, illustrated only by way of non-limitative example in the accompanying drawings, wherein.

WAYS OF CARRYING OUT THE INVENTION

Figure 1:
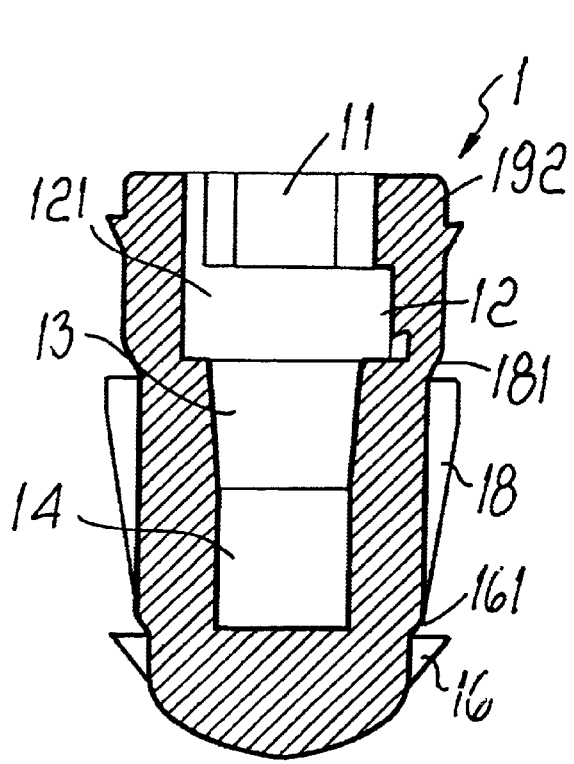
FIG. 1 is a sectional view of the intrabony metallic implant (generally made of titanium) according to the invention with a stump associated therewith.
Figure 3:
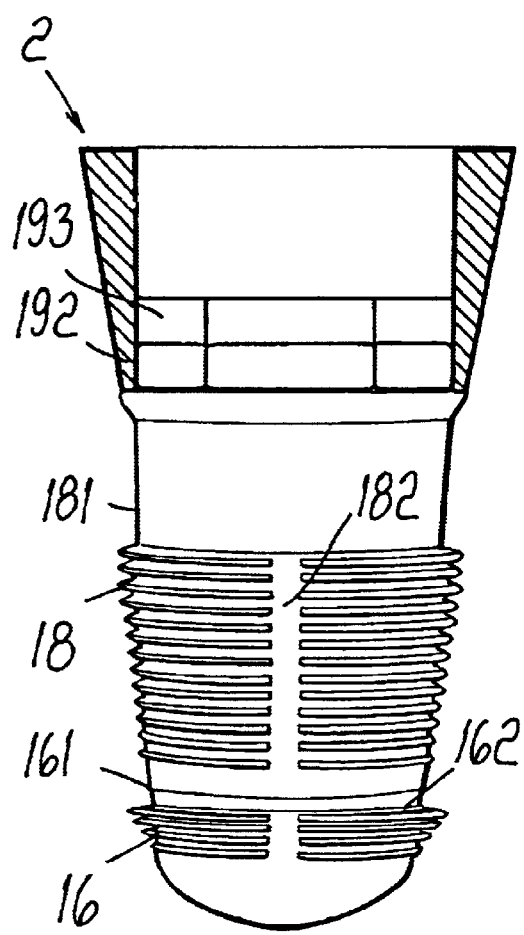
FIG. 3 is a partially sectional view of the intrabony implant of FIG. 1, taken from the outside.
Figure 2:
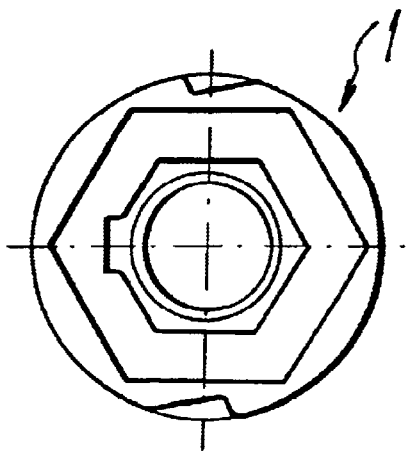
FIG. 2 is a plan view of the intrabony implant of FIG. 1.
Figure 4:
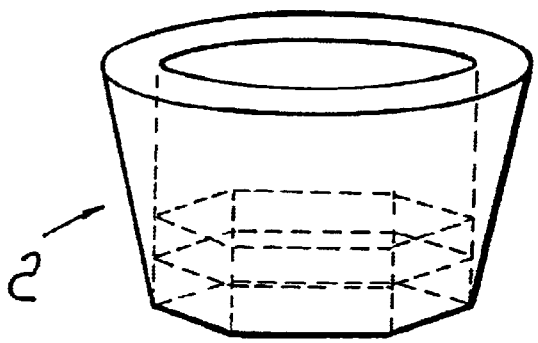
FIG. 4 is a perspective view of the implant according to the invention with a rotation-preventing bush.
Figure 5:
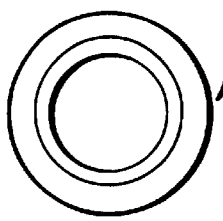
FIGS. 5 and 6 are, respectively, a sectional front view and a top view of an extension ring made of calcinable resin which can be fitted over the intrabony implant.
Figure 7:
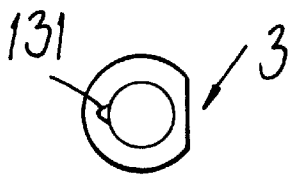
FIGS. 7 and 8 are a front view and a top view of a titanium stump.
Figure 9:
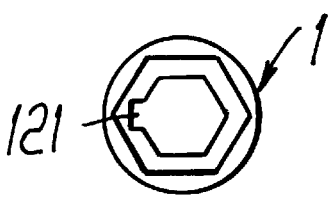
FIGS. 9 and 10 are an axial sectional front view and a top view of a titanium intrabony implant.
Figure 6:
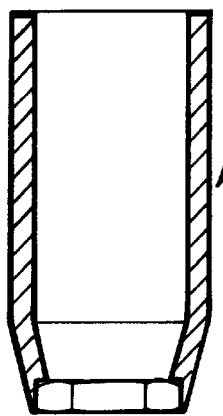
Figure 8:
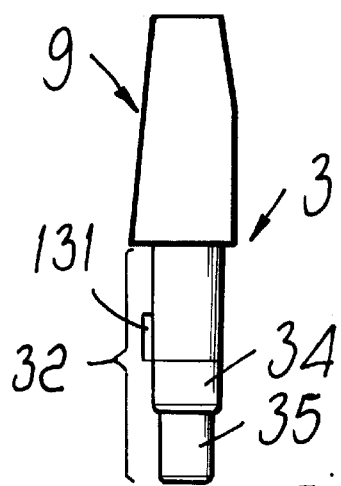
Figure 10:
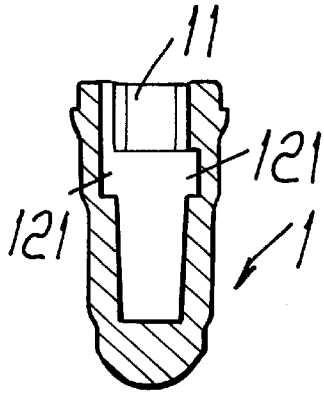
Figure 11:
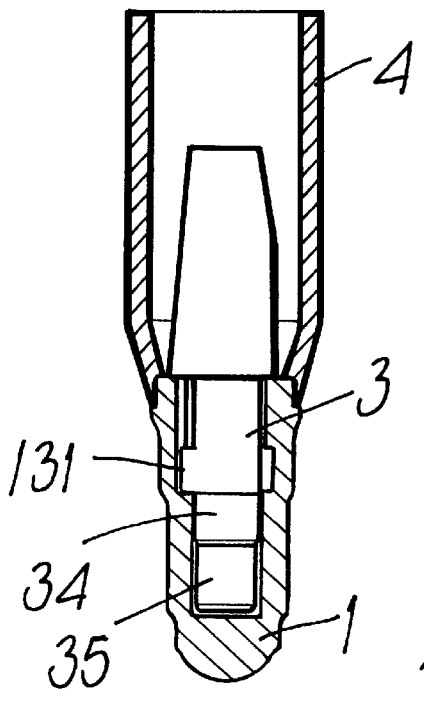
FIG. 11 is a sectional view of the assembly of the components of the intrabony implant in the assembled condition.

With reference to the above FIGS. 1 to 11, in a first embodiment the implant according to the invention comprises a hollow intrabony implant 1 to be inserted in a fixed manner in the jawbone, not shown in the figures, and an artificial tooth assembly which has a stump 3 for the respective artificial tooth, also not shown, with a protrusion 9 for insertion coupling with said artificial tooth and a lower stem 32 for entering a cavity of the intrabony implant 1 for fixing it.

The cavity of the intrabony implant 1 is composed, sequentially from the top downwards, of portions 11, 12, 13 and 14 which will be better described hereinafter.

The cavity is in fact provided with an undercut annular recess 12 and with at least one longitudinal slot 121 which cooperates with at least one lug 131 of the stump 3 in order to provide coupling by axial insertion and subsequent rotation, associated with a beveled locking coupling and with an external polygonal shape of both, in order to fit a rotation-preventing keying ring 2.

In particular, in the cavity of the intrabony implant 1, below the undercut annular recess 12 there are two hole portions having a smaller diameter, respectively a conical portion 13 followed by a cylindrical one 14; above said recess there is a hole portion having a smaller diameter 11 which is interrupted by the longitudinal access slot 121 for the passage of the lug 131 of the stem 32 of said tooth stump 3.

The outer upper end 192 of the intrabony implant 1 is polygonal.

The tooth stump 3 protrudes beyond lug 131 with two portions 34 and 35 which correspond to the portions 13 and 14 of the cavity with which they mate.

The stump 3 is externally provided, above the lug 131, in the part 9 that protrudes beyond the intrabony implant 1, when it is inserted, with a polygonal region 193.

The outer shaped regions 192 and 193, of the intrabony implant 1 and of the stump 3 respectively, are adapted for the coupling of a rotation-preventing locking bush 2 which is shaped internally like a polygonal ring and is suitable to fit around both regions in order to be locked thereat and prevent the mutual rotation of the two parts.

Advantageously, the intrabony outer part of the intrabony implant 1 is sanded and consists of two threaded portions 16 and 18 with two different types of thread in order to facilitate insertion and grip.

Both threaded portions 16 and 18 end, in an upward region, with respective shoulders 161 and 181, each of which is substantially formed by a fishbone wedge so as to improve grip.

Equally advantageously, in the threaded regions there are longitudinal notches 162 and 182 so as to provide correspond cutting edges for the self-tapping of the intrabony implant 1 on the bone during screwing.

It should also be noted that the mating between the portions 13 of the implant 1 and 34 of the stump 3, which are beveled, gives greater safety and solidity to the mating.

Figure 12:
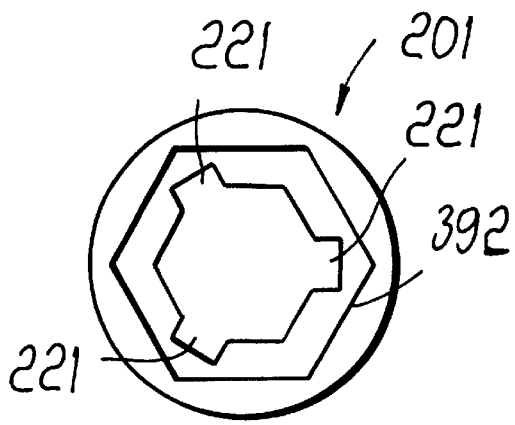
FIGS. 12 and 13 are, respectively, a top view and a longitudinal sectional view of an intrabony implant in another embodiment of the invention.
Figure 14:
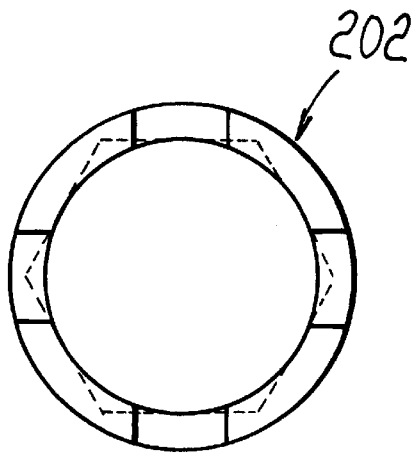
FIGS. 14, 15 and 16 are, respectively, a top view, a sectional view and a side view of an annular rotation-preventing bush.
Figure 13:
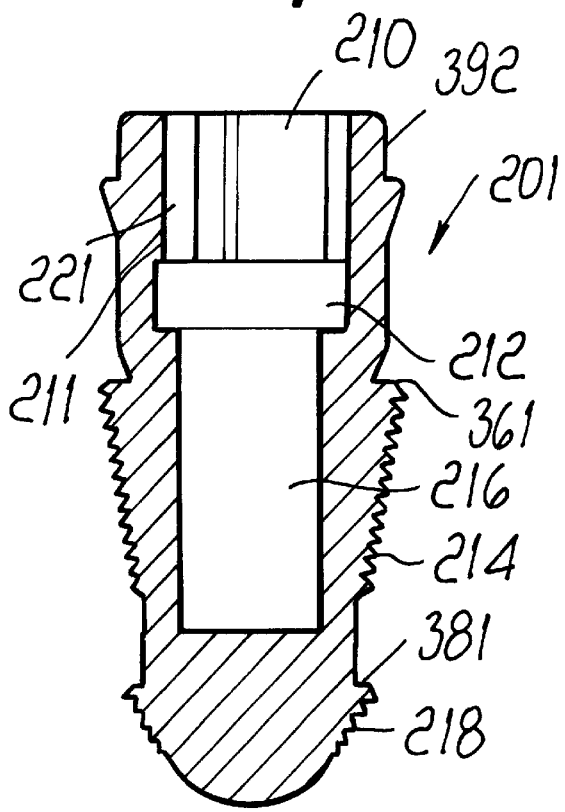
Figure 15:
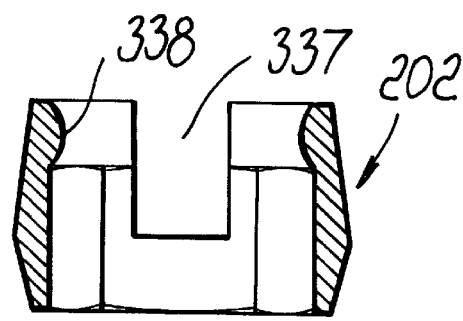
Figure 16:
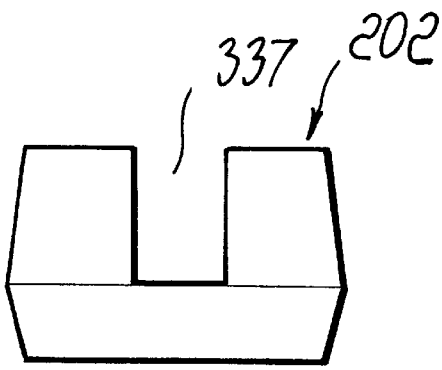
Figure 17:
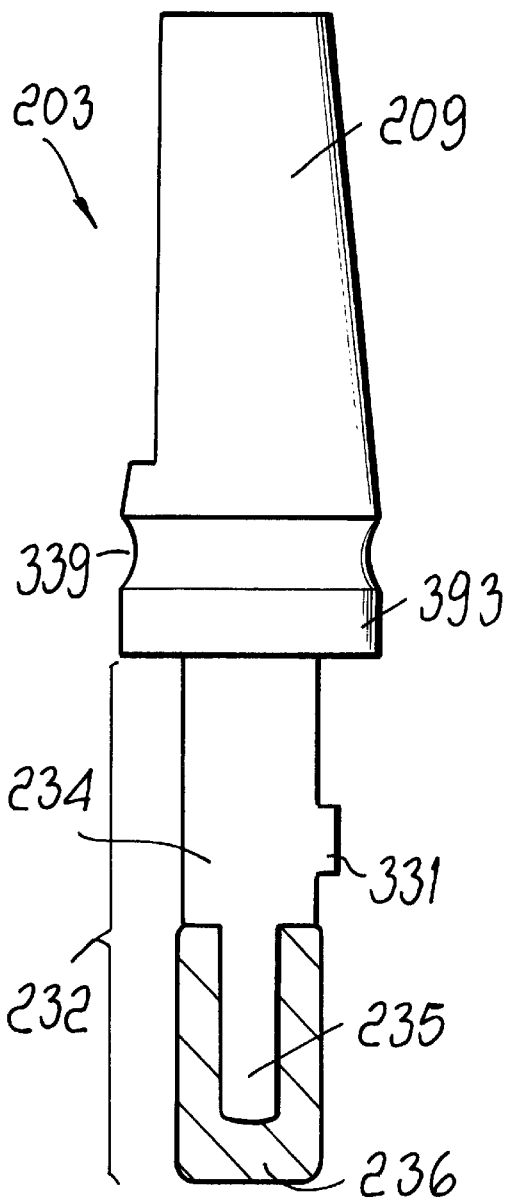
FIG. 17 is a side view of a stump.
Figure 18:
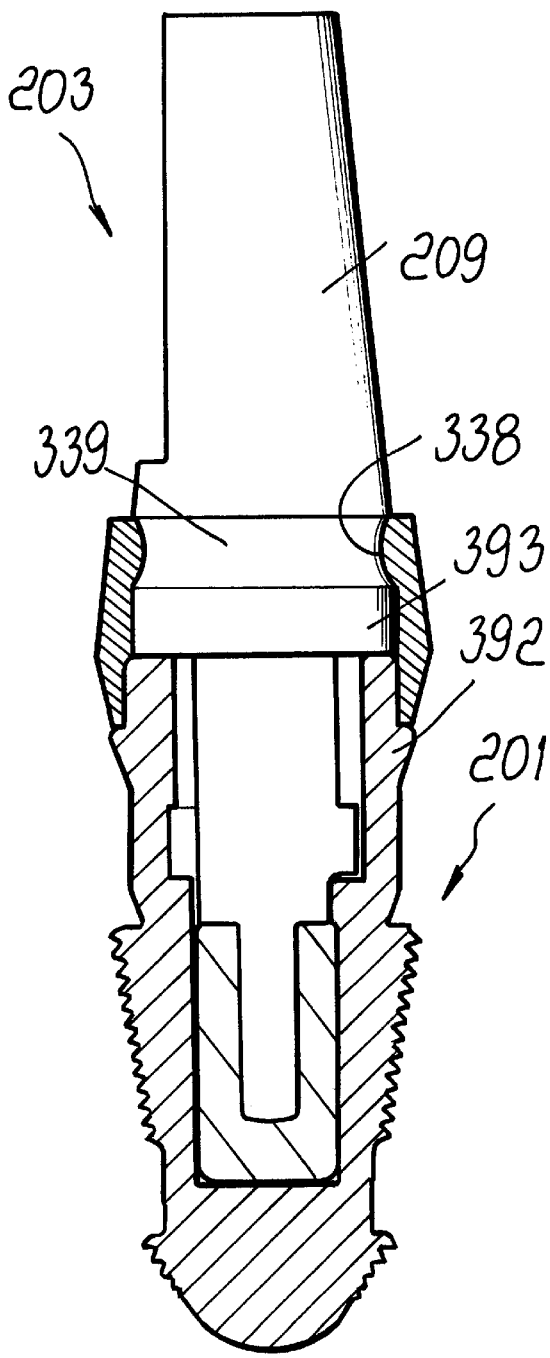
FIG. 18 is a sectional view of the components in the assembled condition.

With reference now to the above cited FIGS. 12 to 18, in another embodiment the implant according to the invention comprises a hollow intrabony implant 201, to be inserted in a fixed manner in the jawbone, not shown in the figures, and an artificial tooth assembly, which has a stump 203 for the respective artificial tooth, also not shown, with a protrusion 209 for engagement with the artificial tooth and a lower stem 232 for entering the cavity 210 of the intrabony implant 201 in order to fix it.

The cavity 210 of the intrabony implant 201 is composed, from the top downwards, of portions 211, 212 and 216 described in detail hereinafter.

The cavity 210 has an undercut annular recess 212 and three longitudinal slots 221 (arranged at 120° to each other), which cooperate with at least one lug 331 of the stump 203, in order to provide coupling by axial insertion and subsequent rotation, associated with a mating by virtue of the external polygonal shape of both parts in order to fit a rotation-preventing keying ring 202.

The cavity 210 of the intrabony implant 201 has an undercut annular recess 212 below which there is a portion 216 of a cylindrical hole which has a smaller diameter and above which there is a hole portion having a smaller diameter 211 which is interrupted by the longitudinal access slot 221 for the passage of a lug 331 of the stem 232 of the tooth stump 203 by axial sliding and subsequent rotation.

The lower part 234 of the stump 203 to be inserted in the cavity 210 has an end part 235 which has a smaller diameter and is covered by a capshaped element 236 made of elastic material (for example Teflon).

The distance between the upper part of the recess 212 and the bottom of the cavity 210 is slightly shorter than the distance between the upper part of the lug 331 and the end of the element 236, so that the latter is slightly compressed upon mating.

Once mating has been provided, the lug 331 is pushed against the upper part of the recess 212 so as to provide rotation-preventing friction.

The outer upper end 392 of the intrabony implant 201 is polygonal.

The tooth stump 203 protrudes beyond the lug 331 with the part 234 that corresponds to the portion 216 of the cavity 210 with which it mates by virtue of the interposition of the element 236.

The stump 203 is externally provided, above lug 331, in the part 209 that protrudes beyond the intrabony implant 201, when inserted, with a polygonal region 393.

The outer shaped regions 392 and 393 of the intrabony implant 201 and of the stump 203, respectively, are adapted for the coupling of a rotation-preventing annular locking bush 202 which is internally polygonal and is adapted to fit over both regions so as to be locked thereat and prevent the mutual rotation of the two parts.

The bush 202 is in fact provided, in an upward region, with notches 337 which allow the flexing of a corresponding part thereof which is internally provided with an annular protruding edge 338 which is adapted to fit with a snap action in a corresponding annular slot 339 of the stump 203.

Advantageously, the intrabony external part of the intrabony implant 201 is formed by two threaded portions 214 and 218 in order to allow easy insertion and grip.

Both threaded portions 214 and 218 end, in an upward region, with respective shoulders 361 and 381, each of which substantially forms a fishbone wedge so as to improve grip.

Equally advantageously, in the threaded regions there are longitudinal notches, not shown in the figures, so as to provide corresponding cutting edges for the self-tapping of the implant 1 on the bone during screwing.

In practice it has been observed that the intended aim of the invention has been achieved, a quick coupling of the bayonet type with axial and rotary motion having been achieved which provides the advantage of adequate safety against loosening and breakage in addition to quick action.

The invention thus conceived is susceptible of numerous modifications and variations, all of which are within the scope of the inventive concept.

All the details may furthermore be replaced with other technically equivalent elements.

In practice, the materials used, as well as the dimensions, may be any according to requirements.

The disclosures in Italian Patent Application No. UD99A000056 from which this application claims priority are incorporated herein by reference.

What is claimed is:

1. An implant assembly, comprising:
    an intrabony implant which is designed to be inserted in a fixed manner in the jawbone and is provided with a cavity;
    an artificial tooth assembly with a tooth stump for the respective artificial tooth, said tooth stump having a lower stem to be inserted and fixed in said cavity of said intrabony implant, and said tooth stump having an upper protrusion for engagement with an artificial tooth;
    wherein said cavity of said intrabony implant has an undercut annular recess below and above which there are hole portions having a smaller diameter, one of said hole portions, above said recess, being interrupted by at least one longitudinal access slot for the passage of at least one lug of the stem of said tooth stump by axial sliding and subsequent rotation of said stem in said recess, the outer upper end of said intrabony implant being polygonal, said tooth stump protruding above said lug with said protrusion having a polygonal region for the insertion of a polygonal annular bush for the mutual locking of said stump with respect to said intrabony implant so as to prevent rotation.

2. The implant assembly according to claim 1, wherein the external part of the intrabony implant is threaded.

3. The implant assembly according to claim 2, wherein said intrabony implant is formed by two conical threaded portions which end, in an upward region, with respective shoulders, each of which substantially forms a fishbone wedge.

4. The implant assembly according to claim 3, wherein in said threaded portions there are longitudinal notches so as to form corresponding cutting edges for the self-tapping of the intrabony implant on the bone during screwing.

5. The implant assembly according to claim 1, wherein the mating between the lower stem of said stump and the corresponding cavity is provided by virtue of complementarily shaped conical parts.

6. The implant assembly according to claim 5, wherein the lower stem of said stump to be inserted in said cavity has an end portion which has a smaller diameter and is covered by a cap-like element made of elastic material, the distance between the upper wall of said undercut recess and the bottom of said cavity being shorter than the distance between the upper part of said lug and the end of the cap-like element, so that the latter is compressed upon mating.

7. The implant assembly according to claim 1, wherein said bush is provided, in an upward region, with notches which allow the flexing of a corresponding part thereof which is internally provided with a raised annular edge which is suitable to fit, with a snap action, in a corresponding annular slot of said stump.

* * * * *